United States Patent [19]

Leppard et al.

[11] Patent Number: 4,465,765
[45] Date of Patent: Aug. 14, 1984

[54] COLORPHOTOGRAPHIC RECORDING MATERIAL

[75] Inventors: David G. Leppard, Marly; Jean Rody, Riehen, both of Switzerland

[73] Assignee: Ciba-Geigy A.G., Basel, Switzerland

[21] Appl. No.: 523,411

[22] Filed: Aug. 16, 1983

[30] Foreign Application Priority Data

Aug. 18, 1982 [CH] Switzerland ............... 4938/82

[51] Int. Cl.$^3$ .................. G03C 1/84; G03C 7/26
[52] U.S. Cl. ........................... 430/512; 430/523; 430/551; 430/17
[58] Field of Search ............ 430/551, 512, 372, 523, 430/17; 524/99

[56] References Cited

U.S. PATENT DOCUMENTS

| | | | |
|---|---|---|---|
| 2,596,926 | 5/1952 | Gunther et al. | 430/372 |
| 3,183,219 | 5/1965 | Schuler | 430/512 |
| 3,960,928 | 6/1976 | Mauz | 560/75 |
| 4,197,236 | 4/1980 | Rosenberger et al. | 524/99 |
| 4,268,593 | 5/1981 | Leppard et al. | 430/551 |

FOREIGN PATENT DOCUMENTS 2126187 12/1971 Fed. Rep. of Germany.
1326889 8/1973 United Kingdom.

Primary Examiner—J. Travis Brown
Attorney, Agent, or Firm—Wenderoth, Lind & Ponack

[57] ABSTRACT

Compounds of the formula I

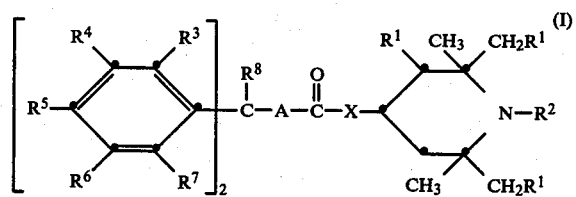

in which A is a direct bond or a substituted or unsubstituted alkylene radical, X is —O— or —N($R^{16}$)—, $R^2$ is a monovalent radical, $R^5$ or $R^3$ is hydroxyl, and $R^1$, $R^4$, $R^6$, $R^7$ and $R^8$ are hydrogen or monovalent radicals, are effective stabilizers for photographic dyes and precursors thereof. In particular, they increase the light fastness of the developed color images.

9 Claims, No Drawings

COLORPHOTOGRAPHIC RECORDING MATERIAL

The present invention relates to a colourphotographic recording material which, in at least one light-sensitive silver halide emulsion layer and/or in at least one of the customary auxiliary layers, contains at least one specific polyalkylpiperidine optical stabiliser.

Polyalkylpiperidines, as sterically hindered amines, are generally known for use as optical stabilisers for organic materials, in particular for polymers. German Offenlegungsschrift No. 2,126,954 in fact has already proposed using such polyalkylpiperidines as agents against the fading of colour photographs. European Pat. No. A 11,051 further proposes using, as optical stabilisers for colour photographs, certain polyalkylpiperidine derivatives which contain at least one phenol group. The derivatives are polyalkylpiperidine esters of hydroxybenzylmalonic acids.

In continuing this research work, it was found that polyalkylpiperidine derivatives of diphenolalkanoic acids likewise have an excellent optical stabilising action for colour photographs and, what is more, also stabilise the dyes against changes under the action of heat or moisture.

The present invention therefore relates to a colourphotographic recording material which, in at least one light-sensitive silver halide emulsion layer, intermediate layer and/or protective layer, contains at least one polyalkylpiperidine compound as an optical stabiliser and wherein the optical stabiliser is a compound of the formula I

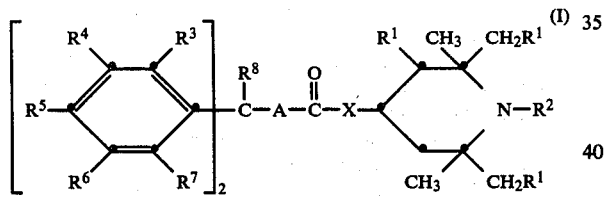

in which $R^1$ is hydrogen or methyl, $R^2$ is hydroxyl, $C_1$–$C_{12}$-alkyl, $C_3$–$C_6$-alkenyl, $C_3$–$C_4$-alkynyl, $C_7$–$C_{12}$-aralkyl, glycidyl, halogen-, cyano-, —$COOR^9$— or —$CON(R^{10})(R^{11})$-substituted $C_1$–$C_4$-alkyl, a —CO—$R^{12}$, —CO—$OR^9$ or —CO—$N(R^{10})(R^{11})$ group, a —$CH_2$—$CH(R^{13})$—$OR^{14}$, —SO—$R^{15}$, —$SO_2$—$R^{15}$, —$OR^9$ or —OOC—$R^{12}$ group, or a group of the formula

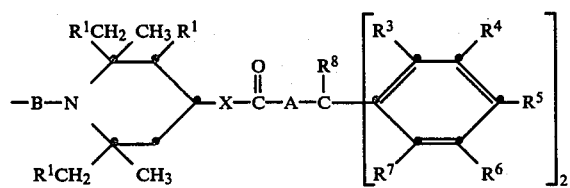

$R^3$ and $R^5$ are hydrogen or hydroxyl in such a way that either $R^3$ is hydrogen and $R^5$ is hydroxyl or $R^3$ is hydroxyl and $R^5$ is hydrogen, $R^4$ is $C_1$–$C_{12}$-alkyl, $C_5$–$C_6$-cycloalkyl, $C_6$–$C_{10}$-aryl or $C_7$–$C_9$-phenylalkyl, $R^6$ and $R^7$, independently of each other, are hydrogen, $C_1$–$C_{12}$-alkyl, $C_5$–$C_8$-cycloalkyl, $C_6$–$C_{10}$-aryl or $C_7$–$C_9$-phenylalkyl, $R^8$ is hydrogen, $C_1$–$C_{12}$-alkyl, $C_5$–$C_8$-cycloalkyl, benzyl or phenyl, $R^9$ is $C_1$–$C_{12}$-alkyl, allyl, cyclohexyl or benzyl, $R^{10}$ is $C_1$–$C_{12}$-alkyl, allyl, cyclohexyl, benzyl, phenyl or $C_7$–$C_{12}$-alkylphenyl, $R^{11}$ is hydrogen, $C_1$–$C_{12}$-alkyl, allyl, cyclohexyl or benzyl, or $R^{10}$ and $R^{11}$, together with the N atom to which they are bonded, form a 5- or 6-membered heterocyclic ring, $R^{12}$ is hydrogen, $C_1$–$C_{12}$-alkyl, $C_2$–$C_6$-alkenyl, chloromethyl, $C_5$–$C_8$-cycloalkyl, $C_7$–$C_{12}$-aralkyl, phenyl, $C_7$–$C_{12}$-alkylphenyl or phenyl, phenylmethyl or phenylethyl which is substituted by 1 or 2 $C_1$–$C_4$-alkyl groups and a hydroxyl group, $R^{13}$ is hydrogen, $C_1$–$C_4$-alkyl, $C_2$–$C_{13}$-alkoxymethyl, phenyl or phenoxymethyl, $R^{14}$ is hydrogen, $C_1$–$C_{12}$-alkyl, a —CO—$R^{12}$ or —CO—$N(R^{10})(R^{11})$ group or a group of the formula II

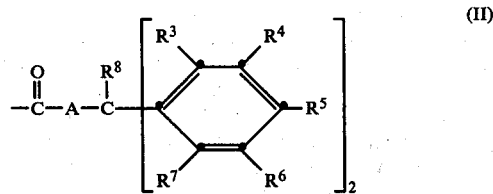

$R^{15}$ is $C_1$–$C_{12}$-alkyl, phenyl or $C_7$–$C_{12}$-alkylphenyl, A is a direct bond or $C_1$–$C_{12}$-alkylene which can be interrupted by —S— or —COO— or be substituted by one of the groups —$SO_2$—$R^{15}$, —CN, —$P(O)(OR^{15})_2$ or

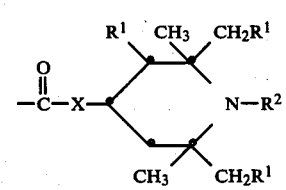

B is $C_2$–$C_{12}$-alkylene, $C_4$–$C_8$-alkenylene, $C_4$–$C_6$-alkynylene or $C_8$–$C_{14}$-aralkylene, and X is —O— or —$N(R^{16})$— in which $R^{16}$ is hydrogen, $C_1$–$C_{18}$-alkyl, $C_5$–$C_{12}$-cycloalkyl or a group of the formula III

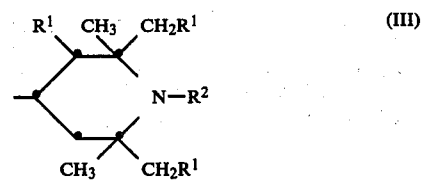

In the compound of the formula I, the $R^2$, $R^4$, $R^6$, $R^7$, $R^8$, $R^9$, $R^{10}$, $R^{11}$, $R^{12}$, $R^{14}$ and $R^{15}$ substituents can be $C_1$–$C_{12}$-alkyl, and as such they can be branched or unbranched alkyl, for example methyl, ethyl, isopropyl, tert.-butyl, isoamyl, n-hexyl, n-octyl, 2-ethylhexyl, 1,1,3,3-tetramethylbutyl, isononyl, n-decyl or n-dodecyl. A $C_1$–$C_{18}$-alkyl $R^{16}$ can additionally also be, for example, tetradecyl, hexadecyl or octadecyl.

An alkenyl $R^2$ can be, for example, allyl, methallyl, dimethylallyl or 2-hexenyl. An alkenyl $R^{12}$ can additionally also be vinyl. An alkynyl $R^2$ can be, for example, 2-propynyl or 2-butynyl.

Cycloalkyls $R^4$, $R^6$, $R^7$, $R^8$ and $R^{12}$ can be, for example, cyclopentyl, cyclohexyl, methylcyclohexyl, dimethylcyclohexyl, cycloheptyl or cyclooctyl. A $C_5$–$C_{12}$-cycloalkyl $R^{16}$ can additionally also be, for example, diethylcyclohexyl or cyclododecyl.

Phenylalkyls $R^4$, $R^6$ and $R^7$ can be, for example, benzyl, phenylethyl or phenylpropyl. Aralkyls $R^2$ and $R^{12}$ can additionally also be phenylbutyl or naphthylmethyl.

Aryls $R^4$, $R^6$ and $R^7$ can be, for example, phenyl or naphthyl. Alkylphenyls $R^{10}$, $R^{12}$ and $R^{15}$ can be, for example, tolyl, xylyl, isopropylphenyl, tert.-butylphenyl or diethylphenyl.

A $C_1$–$C_{12}$-alkylene link A can be unbranched or branched alkylene, for example methylene, 1,2-ethylene, 1,2-propylene, 1,3-propylene, 1,2-butylene, 1,4-butylene, hexamethylene, octamethylene or dodecamethylene. An alkylene A is preferably $C_1$–$C_6$-alkylene, in particular $C_1$–$C_4$-alkylene.

The B link can be $C_2$–$C_{12}$-alkylene and is as such preferably unbranched alkylene, for example 1,2-ethylene, 1,3-propylene, tetramethylene, hexamethylene, oxtamethylene or dodecamethylene. B can also be alkenylene, for example but-2-en-1,4-ylene or hex-3-en-1,6-xylene. B can also be alkynylene, for example but-2-yn-1,4-ylene or hex-3-yn-1,6-ylene. B can also be aralkylene, for example xylylene of bitolylene. $R^{10}$ and $R^{11}$, together with the N atom to which they are bonded, can form a 5- or 6-membered heterocyclic ring. This ring can be, for example, a pyrrolidine, piperidine, morpholine or 4-alkylpiperazine ring.

Preferred optical stabilisers are compounds of the formula I in which $R^1$ is hydrogen, $R^2$ is hydroxyl, $C_1$–$C_4$-alkoxy, acetoxy, $C_1$–$C_4$-alkyl, $C_3$–$C_4$-alkenyl, propargyl, glycidyl, benzyl, —$COOR^9$-substituted methyl or ethyl, a —CO—$R^{12}$, —CO—$OR^9$ or —CO—N($R^{10}$)($R^{11}$) group or a —$CH_2$—CH($R^{13}$)—$OR^{14}$, —SO—$R^{15}$, —$SO_2$—$R^{15}$, —$OR^9$ or —OO—C—$R^{12}$ group, $R^3$ is hydrogen and $R^5$ is hydroxyl, or $R^3$ is hydroxyl and $R^5$ is hydrogen, $R^4$ is $C_1$–$C_8$-alkyl, $R^6$ and $R^7$, independently of each other, are H or $C_1$–$C_8$-alkyl, $R^8$ is hydrogen or $C_1$–$C_{12}$-alkyl, $R^9$ is $C_1$–$C_8$-alkyl, allyl or cyclohexyl, $R^{10}$ is $C_1$–$C_{12}$-alkyl, cyclohexyl or phenyl, $R^{11}$ is hydrogen or $C_1$–$C_{12}$-alkyl, or $R^{10}$ and $R^{11}$, together with the N atom to which they are bonded, form a 6-membered heterocyclic ring, $R^{12}$ is $C_1$–$C_{12}$-alkyl, $C_2$–$C_4$-alkenyl, cyclohexyl, benzyl, phenyl or 2-(3,5-di-tert.-butyl-4-hydroxyl)-ethyl, $R^{13}$ is hydrogen, methyl or phenyl, $R^{14}$ is hydrogen, $C_1$–$C_4$-alkyl, a —CO—$R^{12}$ or —CO—N($R^{10}$)($R^{11}$) group or a group of the formula II, $R^{15}$ is $C_1$–$C_4$-alkyl, phenyl or tolyl, A is a direct bond or $C_1$–$C_6$-alkylene which can be substituted by —CN or a group of the formula IV

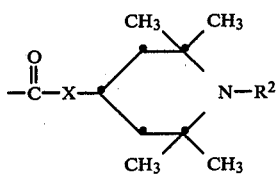

and X is —O— or —NH—.

Preferred optical stabilisers are, in particular, compounds of the formula I in which $R^1$ is hydrogen, $R^2$ is methoxy, methyl, allyl, benzyl, acetyl, acryloyl or a —CO—N($R^{10}$)($R^{11}$), —SO—$R^{15}$ or —$SO_2$—$R^{15}$ group, $R^3$ is hydrogen, $R^4$ is $C_1$–$C_6$-alkyl, $R^5$ is hydroxyl, $R^6$ and $R^7$, independently of each other, are hydrogen or $C_1$–$C_4$-alkyl, $R^8$ is hydrogen or $C_1$–$C_6$-alkyl, $R^{10}$ is $C_1$–$C_8$-alkyl, cyclohexyl or phenyl, $R^{11}$ is hydrogen or $C_1$–$C_8$-alkyl, $R^{15}$ is methyl, phenyl or p-tolyl, A is a direct bond or $C_1$–$C_4$-alkylene which can be substituted by a group of the formula IV, and X is —O— or —NH—.

Particularly preferred optical stabilisers are compounds of the formula I in which $R^1$ is hydrogen, $R^2$ is methoxy, methyl, allyl, benzyl, acetyl, acryloyl or a —CO—N($R^{10}$)($R^{11}$), —SO—$R^{15}$ or —$SO_2R^{15}$ group, $R^3$ is hydrogen, $R^4$ is $C_1$–$C_4$-alkyl, $R^5$ is hydroxyl, $R^6$ is hydrogen or $C_1$–$C_4$-alkyl, $R^7$ and $R^8$ are hydrogen or methyl, $R^{10}$ is $C_1$–$C_4$-alkyl, cyclohexyl or phenyl, $R^{11}$ is hydrogen or $C_1$–$C_4$-alkyl, $R^{15}$ is phenyl or p-tolyl, A is a direct bond or $C_1$–$C_4$-alkylene, and X is —O—, in particular those compounds of the formula I in which $R^1$ is hydrogen, $R^2$ is methyl, allyl, benzyl, acetyl or acryloyl, $R^3$ is hydrogen, $R^4$ is $C_1$–$C_4$-alkyl, $R^5$ is hydroxyl, $R^6$, $R^7$ and $R^8$ are hydrogen or methyl, A is $C_1$–$C_4$-alkylene, and X is —O—.

Some of the compounds of the formula I which are described herein are disclosed by German Offenlegungsschrift No. 2,717,087, where the compounds are described as optical stabilisers for plastics. The Offenlegungsschrift also describes various processes for preparing these compounds. These processes comprise, first of all, reacting diphenylalkanoic acids, or esters or halides thereof, with 4-hydroxypolyalkylpiperidines or 4-aminopolyalkylpiperidines and, secondly, reacting aliphatic ketocarboxylates or ketocarboxamides of 4-hydroxypolyalkylpiperidines or 4-aminopolyalkylpiperidines with phenols in accordance with the process of German Offenlegungsschrift No. 1,953,333.

The $R^2$ substituent can be introduced at various stages of the preparation by substituting the corresponding NH compounds by the methods known in general for the N-substitution of secondary amines.

Insofar as the compounds of the formula I described herein do not belong to the compounds described in German Offenlegungsschrift No. 2,717,087, they can be prepared analogously. Further details on this point can be taken from the preparation examples which follow below.

Examples of individual compounds of the formula I, which, according to the invention, can be used as optical stabilisers for colourphotographic recording material, are the following compounds:

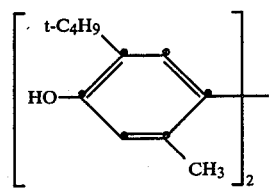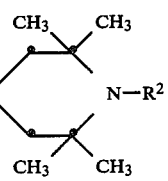

No. 1 $R^2 = $ —$CH_3$
No. 2 $R^2 = $ —CO—$CH_3$

-continued
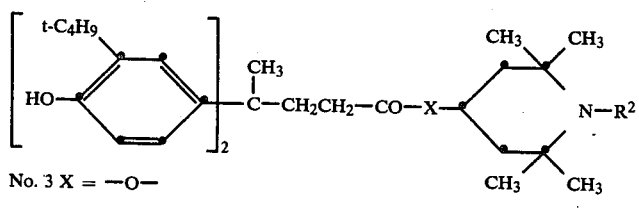
No. 3 X = —O—
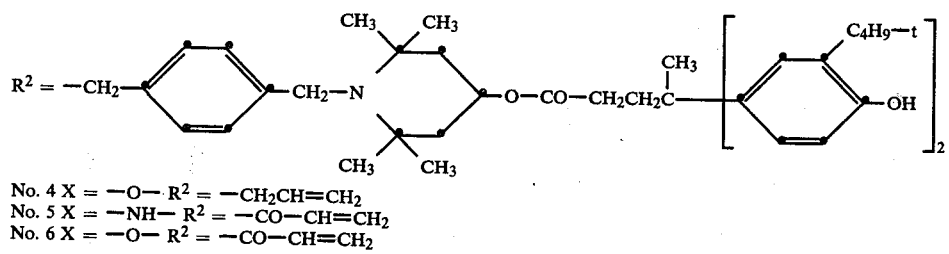
No. 4 X = —O— R² = —CH₂CH=CH₂
No. 5 X = —NH— R² = —CO—CH=CH₂
No. 6 X = —O— R² = —CO—CH=CH₂
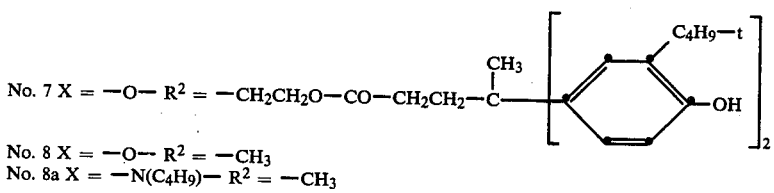
No. 7 X = —O— R² = —CH₂CH₂O—CO—CH₂CH₂—
No. 8 X = —O— R² = —CH₃
No. 8a X = —N(C₄H₉)— R² = —CH₃
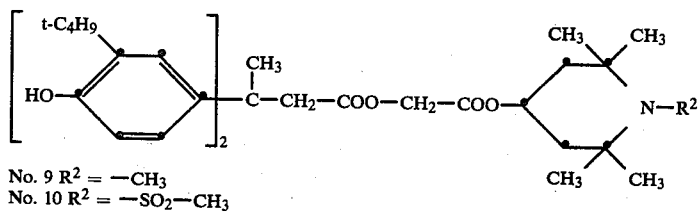
No. 9 R² = —CH₃
No. 10 R² = —SO₂—CH₃
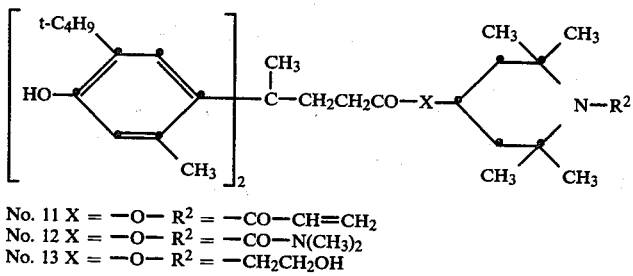
No. 11 X = —O— R² = —CO—CH=CH₂
No. 12 X = —O— R² = —CO—N(CH₃)₂
No. 13 X = —O— R² = —CH₂CH₂OH
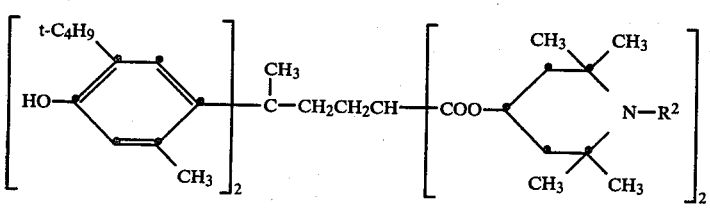
No. 14 R = —CO—CH=CH₂
No. 15 R = —CH₃

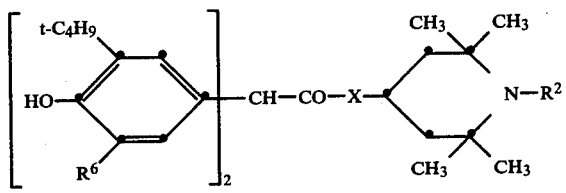

No. 16 X = —O— R² = CH₃ R⁶ = t-C₄H₉
No. 17 X = —O— R² = benzyl R⁶ = t-C₄H₉
No. 18 X = —O— R² = —CO—CH₃ R⁶ = t-C₄H₉
No. 19 X = —O— R² = —CO—CH₃ R⁶ = CH₃
No. 20 X = —O— R² = —CO—CH=CH₂ R⁶ = t-C₄H₉
No. 21 X = —O— R² = —OCH₃ R⁶ = t-C₄H₉
No. 22 X = —O— R² = —CO—N(C₂H₅)₂ R⁶ = CH₃

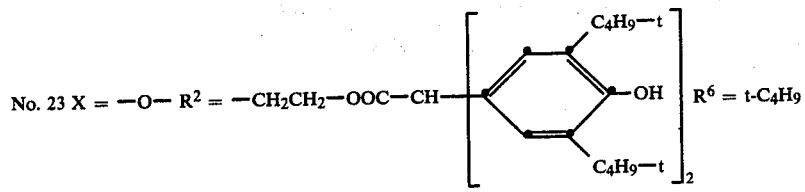

No. 23 X = —O— R² = —CH₂CH₂—OOC—CH— ... R⁶ = t-C₄H₉

The compounds of the formula I are barely soluble in water, and for this reason they are preferably added to the photographic layers in the form of a dispersion or emulsion. As a rule, the stabilisers are incorporated into the photographic material together with the colour couplers.

For this purpose, the compounds of the formula I, together with the colour couplers and, if desired, with further optical stabilisers, are dissolved in a low-boiling organic solvent, such as methyl acetate, ethyl acetate, carbon tetrachloride, chloroform, methanol, ethanol, n-butanol, dioxane, acetone or benzene, a high-boiling organic solvent, such as tricresyl phosphate, dimethylformamide, dimethyl sulfoxide, di-n-butyl phthalate or ethyl N-diphenylcarbamate, or a solvent mixture of the abovementioned low-boiling and high-boiling organic solvents, the solution obtained is added to a protective colloid solution, such as, in particular, an aqueous gelatin solution, and the solution is dispersed therein by means of a colloid mill, a homogeniser or ultrasound.

The dispersions thus obtained are then used for preparing the layers of colourphotographic recording materials. These layers can be, for example, intermediate or protective layers, but in particular light-sensitive (blue-, green- and red-sensitive) silver halide emulsion layers in which the bluish green (cyan), purple (magenta) and yellow dyes are formed from the corresponding colour couplers as the exposed recording material is developed.

If desired, the optical stabiliser can also be applied in the treatment baths which are used after the colour-developing, for example in fixing and/or washing baths, but it is necessary for the compounds of the formula I to have a certain solubility in alcohols (methanol/ethanol), aqueous alkali or water. If the diffusion transfer method is used, the optical stabiliser can also be incorporated into a receiving layer.

The silver halide layers can contain any colour couplers, in particular cyan, magenta and yellow couplers, which are used to form said dyes and hence the colour images.

In the photographic recording material of the present invention, the optical stabilisers of the formula I can be combined in the same layer, in addition to the colour couplers, also with ultraviolet absorbers or other optical stabilisers.

The silver halide emulsions preferably contain, as a binder, gelatin, if desired as a mixture with other high molecular weight natural or synthetic compounds.

The silver halide emulsions can be, for example, silver bromide, silver chloride or silver iodide emulsions or even such emulsions as contain a mixture of silver halides, for example silver bromide iodide or silver chloride bromide emulsions.

The emulsions can be chemically sensitised, and they can also contain customary organic stabilisers and antifogging agents and also customary plasticisers, for example glycerol. The emulsions can also be hardened by means of the hardening agents customary for gelatin. The emulsions can also contain customary casting aids. The emulsions can be applied to supports customary for photographic recording material.

It is possible to use customary developer baths to develop the colourphotographic recording material. These baths generally contain a developer substance of the p-phenylenediamine type, a developing retarder, such as potassium bromide, an antioxidant, such as sodium sulfite or hydroxylamine, and a base, for example an alkali metal hydroxide or alkali metal carbonate. The developing baths can also contain customary antifogging agents and complexing agents.

The optical stabilisers to be used according to the invention are, in certain cases, also suitable for protecting colourphotographic layers in which the dyes are incorporated directly into the emulsion and the image is generated by selective bleaching.

The amount of the optical stabiliser(s) can vary within wide limits and is approximately within the range from 1 to 2,000 mg, preferably 100 to 800 and in particular 200–500, mg per m² of the layer into which it (or they) is (or are) incorporated.

If the photographic material contains an agent which absorbs UV radiation, this agent can be present together with the optical stabiliser in one layer or in an adjacent layer. The weight ratio between the ultraviolet absorber and the optical stabiliser of the formula I is about (2-10):1, the molar ratio being about (5-20):1. Examples of ultraviolet absorbers are compounds of the benzophenone, acrylonitrile, thiazolidone, benzotriazole, oxazole, thiazole and imidazole type.

The colour images obtained by exposing and developing the recording material of the invention have very good light fastness to visible and ultraviolet light. The compounds of the formula I are virtually colourless, so that the images are not discoloured; they are also highly compatible with the customary photographic additives present in the individual layers. Owing to their high effectiveness, it is possible to reduce their level and thus to avoid their precipitating or crystallising when they are incorporated in the form of an organic solution into the aqueous binder emulsions which are used for preparing photographic layers. The optical stabilisers have no adverse effect on the individual processing steps necessary for preparing the colour images after the photographic recording material has been exposed. Furthermore, the phenomenon of pressure fogging, which can frequently arise in the case of blue-sensitive emulsions, can be largely suppressed. Pressure fogging can arise, for example, when photographic materials (silver halide emulsion layers which are present on a support made of natural or synthetic materials) are subjected to mechanical stresses, for example twisting, bending or rubbing, in the course of preparation or in the course of the treatment before the developing (T. H. James, The Theory of Photographic Process 4th edition, Macmillan, New York, N.Y., 1977, page 23 et seq., page 166 et seq.).

The following examples illustrate the present invention without limiting it. In these examples the temperature is given in °C.

EXAMPLES OF PREPARING THE OPTICAL STABILISERS

Example 1

8.5 g (0.02 mol) of ethyl 4,4-bis-(3-tert.-butyl-4-hydroxyphenyl)-valerate and 3.1 g (0.02 mol) of 4-hydroxy-2,2,6,6-tetramethylpiperidine are dissolved in 200 ml of xylene. 0.1 g of dibutyltin oxide is added, and the mixture is heated at the boil under nitrogen for about 6 hours, during which the resulting ethanol is distilled off continuously. When no more ethanol distils off, the reaction solution is cooled down to room temperature, is admixed with 200 ml of water and is efficiently mixed. The organic phase is separated off, is dried over magnesium sulfate and is evaporated. The resulting oil is purified by column chromatography to give 2,2,6,6-tetramethylpiperidin-4-yl 4,4-bis-(3-tert.-butyl-4-hydroxyphenyl)-valerate in the form of a colourless solid having a melting point of 100°.

The procedure described in Example 1 is repeated using an appropriate amount of 1-allyl-4-hydroxy-2,2,6,6-tetramethylpiperidine in plate of 4-hydroxy-2,2,6,6-tetramethylpiperidine. 1-Allyl-2,2,6,6-tetramethylpiperidin-4-yl 4,4-bis-(3-tert.-butyl-4-hydroxyphenyl)-valerate having a melting point of 75° is obtained (optical stabiliser No. 4).

1-Methyl-2,2,6,6-tetramethylpiperidin-4-yl 4,4-bis-(3-tert.-butyl-4-hydroxyphenyl)-valerate, melting point 197° (optical stabiliser No. 8), and the optical stabilisers of the following formulae are prepared analogously:

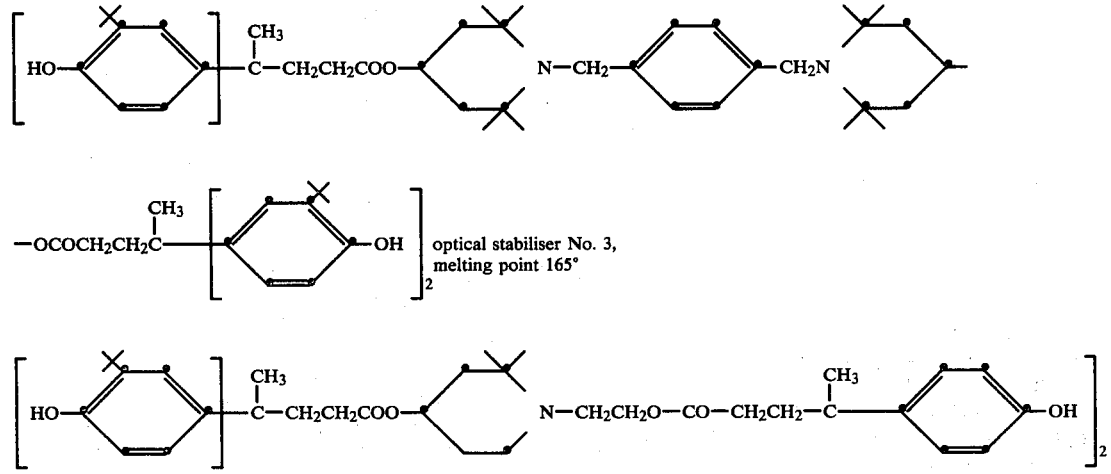

optical stabiliser No. 7, melting point 200°.

Methyl bis-(3,5-di-tert.-butyl-4-hydroxyphenyl)-acetate and the appropriate 4-hydroxypiperidines produce analogously the 1,2,2,6,6-pentamethylpiperidin-4-yl ester of bis-(3,5-di-tert.-butyl-4-hydroxyphenyl)-acetic acid having a melting point of 149° (optical stabiliser No. 16) the 1-benzyl-2,2,6,6-tetramethylpiperidin-4-yl ester having a melting point of 138° (optical stabiliser No. 17) and the diester of the formula

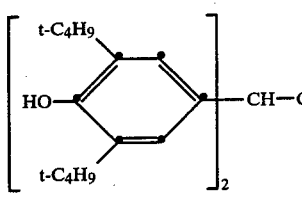 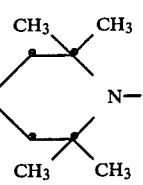 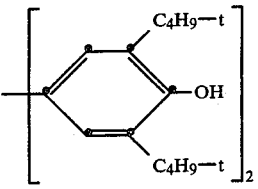

which melts at 237° (stabiliser No. 23).

Methyl 3,3-bis-(3-tert.-butyl-4-hydroxybenzyl)-butyrate produces analogously the corresponding 1,2,2,6,6-pentamethylpiperidin-4-yl ester having a melting point of 110° (optical stabiliser No. 9).

Example 2

Reacting ethyl 4,4-bis-(3-tert.-butyl-4-hydroxyphenyl)-valerate analogously with 4-amino-2,2,6,6-tetramethylpiperidine produces 4-[4,4-bis-(3-tert.-butyl-4-hydroxyphenyl)-valeramido]-2,2,6,6-tetramethylpiperidine having a melting point 133°.

2.7 g of this compound (0.005 mol) are dissolved in 80 ml of ethyl acetate. 0.6 g (0.006 mol) of triethylamine is added, the solution is cooled down to −5°, and a solution of 0.55 g (0.006 mol) of acryloyl chloride in 10 ml of ethyl acetate is added dropwise. The mixture is stirred at −5° for a further 3 hours and is warmed to room temperature. 5 ml of methanol are added, and the solution is washed with water, is dried over magnesium sulfate, and is evaporated. The resulting oil is purified by column chromatography to give 4-[4,4-bis-(3-tert.-butyl-4-hydroxyphenyl)-valeramido]-1-acroyl-2,2,6,6-tetramethylpiperidine having a melting point of 110° (optical stabiliser No. 5).

The procedure described above is repeated, using an appropriate amount of 2,2,6,6-tetramethylpiperidin-4-yl 4,4-bis-(3-tert.-butyl-4-hydroxyphenyl)-valerate in place of 4-[4,4-bis-(3-tert.-butyl-4-hydroxyphenyl)-valeramido]-2,2,6,6-tetramethylpiperidine. 1-Acroyl-2,2,6,6-tetramethylpiperidin-4-yl 4,4-bis-(3-tert.-butyl-4-hydroxyphenyl)-valerate having a melting point of 95° (optical stabiliser No. 6) is obtained.

the procedure described above is repeated using an appropriate amount of bis-(2,2,6,6-tetramethylpiperidin-4-yl) 3,3-bis-(3-tert.-butyl-6-methyl-4-hydroxyphenyl)-butylmalonate in place of 4-[4,4-bis-(3-tert.-butyl-4-hydroxyphenyl)-valeramido]-2,2,6,6-tetramethylpiperidine. bis-(1-Acroyl-2,2,6,6-tetramethylpiperidin-4-yl) [3,3-bis-(3-tert.-butyl-6-methyl-4-hydroxyphenyl)-butyl]-malonate is obtained as a slightly yellow oil (optical stabiliser No. 14).

Example 3

10 g of 2,2,6,6-tetramethyl-4-[3,3-bis-(3-tert.-butyl-6-methyl-4-hydroxyphenyl)-propionyloxy]-piperidine are stirred in 25 ml of acetic anhydride at 110° for 6 hours. The acetic acid formed and excess anhydride are then distilled off under vacuum as completely as possible. The residue is cooled down to room temperature, 100 ml of water are added and are mixed in efficiently, and the precipitate is filtered off, is washed with water and is dried. Crystallising from acetonitrile gives 1-acetyl-2,2,6,6-tetramethyl-4-[3,3-bis-(3-tert.-butyl-6-methyl-4-hydroxyphenyl)-propionyloxy]-piperidine having a melting point of 270° (optical stabiliser No. 2).

The 1-acetyl-2,2,6,6-piperidin-4-yl ester of bis-(3,5-di-tert.-butyl-4-hydroxyphenyl)-acetic acid is obtained analogously with a melting point of 198° (stabiliser No. 18).

APPLICATION EXAMPLES

Example A 0.087 g of the yellow coupler of the formula

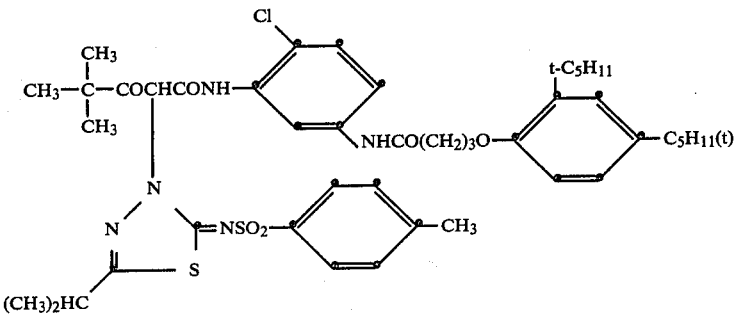

and 0.026 g of one of the optical stabilisers given in the tables below are dissolved in 2.0 ml of a tricresyl phosphate/ethyl acetate mixture (1.5 g in 100 ml). 7.0 ml of a 6% gelatin solution, 0.5 ml of an 8% solution of the wetting agent of the formula

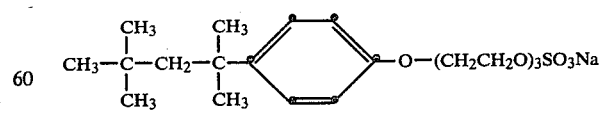

in isopropanol/water (3:4) and 0.5 ml of water are added to the solution and are emulsified therein by means of 100-watt ultrasound for 5 minutes.

2.0 ml of a silver bromide emulsion containing 6.0 g of silver per liter, 0.7 ml of a 1% aqueous solution of the hardening agent of the formula

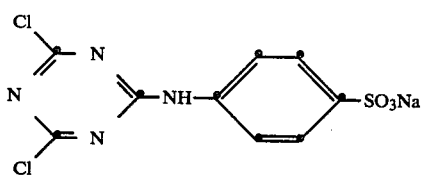

and 3.8 ml of water are added to 2.5 ml of the emulsion thus obtained, and the mixture is brought to pH 6.5 and is then cast onto white subbed plastic-coated paper stretched over a glass plate.

When the cast material has solidified, it is dried in a drying cabinet at room temperature by means of circulating air.

7 days later, samples cut to 35×180 mm are exposed under a step wedge with 3,000 lux.s and are then processed in Kodak's Ektaprint 2 ® process.

The yellow wedges thus obtained are irradiated in an Atlas Weather-Ometer by means of a 2,500-W xenon lamp to a total of 42 kJoule/cm² (a comparative sample contains no optical stabiliser).

Table 1 shows the percentage decreases in colour density from an original density of 1.0.

TABLE 1

| Optical stabiliser No. | Maximum Loss of density in percent (reflectance) |
|---|---|
| none | 41 |
| 2 | 20 |
| 3 | 16 |
| 4 | 18 |
| 5 | 19 |
| 6 | 17 |
| 7 | 19 |
| 8 | 19 |
| 9 | 18 |
| 14 | 20 |

Example B

Samples are prepared as in Example 1, except that in each case 0.042 mmol of the optical stabiliser in cast together with the coupler.

The samples are then irradiated in an Atlas Weather-Ometer under a UV filter (Kodak, 2C grade) to a total of 63 kJoule/cm². Table 2 shows the resulting percentage decreases in density at the maximum in reflectance.

TABLE 2

| Optical stabiliser No. | Loss of density at the maximum in reflectance, in percent |
|---|---|
| none | 15 |
| 5 | 8 |
| 9 | 6 |

It is evident from Examples A and B that the optical stabilisers of the present invention markedly improve the light fastness of a chromogenic yellow dye.

Example C 0.025 g of the cyan coupler of the formula

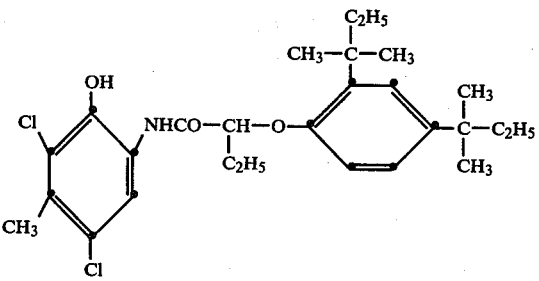

and 0.04 mmol of an optical stabiliser from the table below are dissolved in 1 ml of a mixture of tricresyl phosphate/ethyl acetate (1.5 g in 100 ml). 7.0 ml of a 6% gelatin solution, 0.5 ml of an 8% solution of the wetting agent of the formula

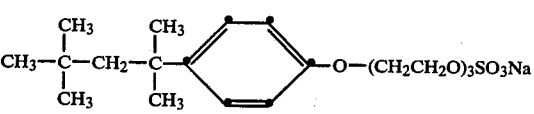

in isopropanol/water (3:4) and 0.5 ml of water are added to the solution and are emulsified therein by means of 100-watt ultrasound for 5 minutes.

2.0 ml of a silver bromide emulsion containing 6.0 g of silver per liter, 0.7 ml of a 1% aqueous solution of the hardening agent of the formula

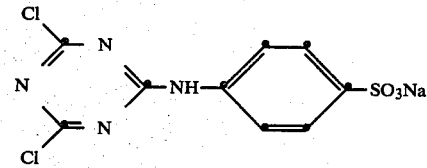

and 3.8 ml of water are added to 2.5 ml of the emulsion thus obtained, and the mixture is brought to pH 6.5 and is cast onto white subbed plastic-coated paper stretched over a glass plate.

When the cast material has solidified, it is dried in a drying cabinet at room temperature by means of circulating air.

The layers are prepared, exposed and processed, all three steps being carried out analogously to the method described in Examples A and B.

The wedges obtained are stored in a conditioning cabinet at 60° C. and 70% relative humidity. The following table shows the percentage decrease in cyan density from an original colour density of 1.0 for red (measurement by means of a ®TR 924 status A densitometer from Macbeth).

TABLE 3

| Optical stabiliser No. | Loss of density in red in percent (D = 1.0, 60° C./70% RH) | |
|---|---|---|
| | 14 days | 28 days |
| none | 24 | 42 |
| 2 | 14 | 23 |
| 17 | 13 | 23 |
| 18 | 9 | 19 |

It can be seen that the stabilisers of the present Application markedly improve the atmospheric stability of a chromogenic cyan dye.

What is claimed is:

1. A colourphotographic recording material which, in at least one light-sensitive silver halide emulsion layer, intermediate layer and/or protective layer, contains at least one polyalkylpiperidine compound as an optical stabiliser, wherein the optical stabiliser is a compound of the formula I

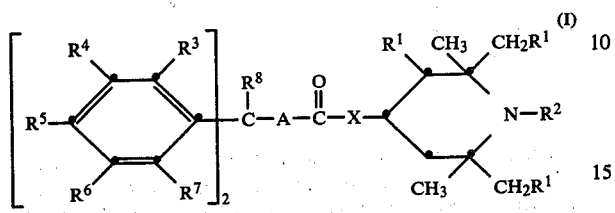

in which $R^1$ is hydrogen or methyl, $R^2$ is hydroxyl, $C_1$-$C_{12}$-alkyl, $C_3$-$C_6$-alkenyl, $C_3$-$C_4$-alkynyl, $C_7$-$C_{12}$-aralkyl, glycidyl, halogen-, cyano-, —COOR$^9$— or —CON($R^{10}$)($R^{11}$)-substituted $C_1$-$C_4$-alkyl, a —CO—$R^{12}$, —CO—OR$^9$ or —CO—N($R^{10}$)($R^{11}$) group, a —CH$_2$—CH($R^{13}$)—OR$^{14}$, —SO—$R^{15}$, —SO$_2$—$R^{15}$, —OR$^9$ or —OOC—$R^{12}$ group, or a group of the formula

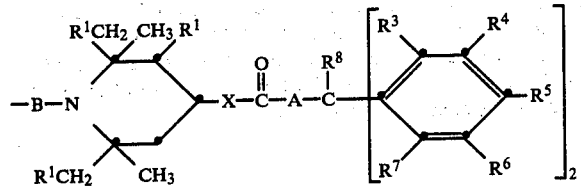

$R^3$ and $R^5$ are hydrogen or hydroxyl in such a way that either $R^3$ is hydrogen and $R^5$ is hydroxyl or $R^3$ is hydroxyl and $R^5$ is hydrogen, $R^4$ is $C_1$-$C_{12}$-alkyl, $C_5$-$C_8$-cycloalkyl, $C_6$-$C_{10}$-aryl or $C_7$-$C_9$-phenylalkyl, $R^6$ and $R^7$, independently of each other, are hydrogen, $C_1$-$C_{12}$-alkyl, $C_5$-$C_8$-cycloalkyl, $C_6$-$C_{10}$-aryl or $C_7$-$C_9$-phenylalkyl, $R^8$ is hydrogen, $C_1$-$C_{12}$-alkyl, $C_5$-$C_8$-cycloalkyl, benzyl or phenyl, $R^9$ is $C_1$-$C_{12}$-alkyl, allyl, cyclohexyl or benzyl, $R^{10}$ is $C_1$-$C_{12}$-alkyl, allyl, cyclohexyl, benzyl, phenyl or $C_7$-$C_{12}$-alkylphenyl, $R^{11}$ is hydrogen, $C_1$-$C_{12}$-alkyl, allyl, cyclohexyl or benzyl, or $R^{10}$ and $R^{11}$, together with the N atom to which they are bonded, form a 5- or 6-membered heterocyclic ring, $R^{12}$ is hydrogen, $C_1$-$C_{12}$-alkyl, $C_2$-$C_6$-alkenyl, chloromethyl, $C_5$-$C_8$-cycloalkyl, $C_7$-$C_{12}$-aralkyl, phenyl, $C_7$-$C_{12}$-alkylphenyl or phenyl, phenylmethyl or phenylethyl which is substituted by 1 or 2 $C_1$-$C_4$-alkyl groups and a hydroxyl group, $R^{13}$ is hydrogen, $C_1$-$C_4$-alkyl, $C_2$-$C_{13}$-alkoxymethyl, phenyl or phenoxymethyl, $R^{14}$ is hydrogen, $C_1$-$C_{12}$-alkyl, a —CO—$R^{12}$ or —CO—N($R^{10}$)($R^{11}$) group or a group of the formula II

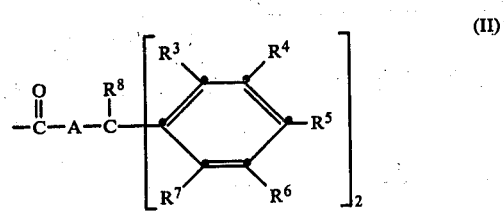

$R^{15}$ is $C_1$-$C_{12}$-alkyl, phenyl or $C_7$-$C_{12}$-alkylphenyl, A is a direct bond or $C_1$-$C_{12}$-alkylene which can be interrupted by —S— or —COO— or be substituted by one of the groups —SO$_2$—$R^{15}$, —CN, —P(O)(OR$^{15}$)$_2$ or

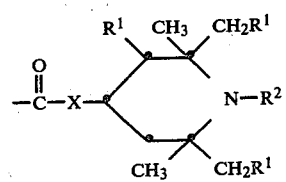

B is $C_2$-$C_{12}$-alkylene, $C_4$-$C_8$-alkenylene, $C_4$-$C_6$-alkynylene or $C_8$-$C_{14}$-aralkylene, and X is —O— or —N($R^{16}$)— in which $R^{16}$ is hydrogen, $C_1$-$C_{18}$-alkyl, $C_5$-$C_{12}$-cycloalkyl or a group of the formula III

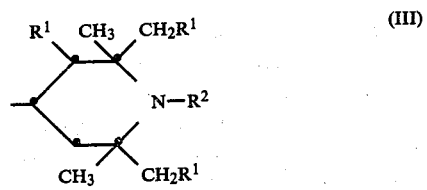

2. A colourphotographic recording material according to claim 1, wherein the optical stabiliser is a compound of the formula I in which $R^1$ is hydrogen, $R^2$ is hydroxyl, $C_1$-$C_4$-alkoxy, acetoxy, $C_1$-$C_4$-alkyl, $C_3$-$C_4$-alkenyl, propargyl, glycidyl, benzyl, —COOR$^9$-substituted methyl or ethyl, a —CO—$R^{12}$, —CO—OR$^9$ or —CO—N($R^{10}$)($R^{11}$) group or a —CH$_2$—CH($R^{13}$)—OR$^{14}$, —SO—$R^{15}$, —SO$_2$—$R^{15}$, —OR$^9$ or —OOC—$R^{12}$ group, $R^3$ is hydrogen and $R^5$ is hydroxyl, or $R^3$ is hydroxyl and $R^5$ is hydrogen, $R^4$ is $C_1$-$C_8$-alkyl, $R^6$ and $R^7$, independently of each other, are H or $C_1$-$C_8$-alkyl, $R^8$ is hydrogen or $C_1$-$C_{12}$-alkyl, $R^9$ is $C_1$-$C_8$-alkyl, allyl or cyclohexyl, $R^{10}$ is $C_1$-$C_{12}$-alkyl, cyclohexyl or phenyl, $R^{11}$ is hydrogen or $C_1$-$C_{12}$-alkyl, or $R^{10}$ and $R^{11}$, together with the N atom to which they are bonded, form a 6-membered heterocyclic ring, $R^{12}$ is $C_1$-$C_{12}$-alkyl, $C_2$-$C_4$-alkenyl, cyclohexyl, benzyl, phenyl or 2-(3,5-di-tert.-butyl-4-hydroxyl)-ethyl, $R^{13}$ is hydrogen, methyl or phenyl, $R^{14}$ is hydrogen, $C_1$-$C_4$-alkyl, a —CO—$R^{12}$ or —CO—N($R^{10}$)($R^{11}$) group or a group of the formula II, $R^{15}$ is $C_1$-$C_4$-alkyl, phenyl or tolyl, A is a direct bond or $C_1$-$C_6$-alkylene which can be substituted by —CN or a group of the formula IV

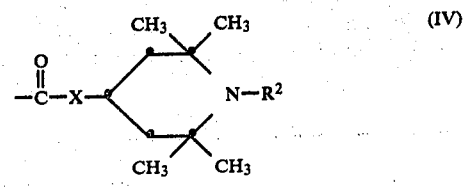

and X is —O— or —NH—.

3. A colourphotographic recording material according to claim 1, wherein the optical stabiliser is a compound of the formula I in which $R^1$ is hydrogen, $R^2$ is methoxy, methyl, allyl, benzyl, acetyl, acryloyl or a —CO—N($R^{10}$)($R^{11}$), —SO—$R^{15}$ or —SO$_2$—$R^{15}$ group, $R^3$ is hydrogen, $R^4$ is $C_1$-$C_6$-alkyl, $R^5$ is hydroxyl, $R^6$ and $R^7$, independently of each other, are hydrogen or $C_1$-$C_4$-alkyl, $R^8$ is hydrogen or $C_1$-$C_6$-alkyl, $R^{10}$ is $C_1$-$C_8$-alkyl, cyclohexyl or phenyl, $R^{11}$ is hydrogen or $C_1$-$C_8$-alkyl, $R^{15}$ is methyl, phenyl or p-tolyl, A is a direct bond or $C_1$–$C_4$-alkylene which can be substituted by a group of the formula IV, and X is —O— or —NH—.

4. A colourphotographic recording material according to claim 1, wherein the optical stabiliser is a compound of the formula I in which $R^1$ is hydrogen, $R^2$ is methoxy, methyl, allyl, benzyl, acetyl, acryloyl or a —CO—N($R^{10}$)($R^{11}$), —SO—$R^{15}$ or —SO$_2$—$R^{15}$ group, $R^3$ is hydrogen, $R^4$ is $C_1$–$C_4$-alkyl, $R^5$ is hydroxyl, $R^6$ is hydrogen or $C_1$–$C_4$-alkyl, $R^7$ and $R^8$ are hydrogen or methyl, $R^{10}$ is $C_1$–$C_4$-alkyl, cyclohexyl or phenyl, $R^{11}$ is hydrogen or $C_1$–$C_4$-alkyl, $R^{15}$ is phenyl or p-tolyl, A is a direct bond or $C_1$–$C_4$-alkylene, and X is —O—.

5. A colourphotographic recording material according to claim 1, wherein the optical stabiliser is a compound of the formula I in which $R^1$ is hydrogen, $R^2$ is methyl, allyl, benzyl, acetyl or acryloyl, $R^3$ is hydrogen, $R^4$ is $C_1$–$C_4$-alkyl, $R^5$ is hydroxyl, $R^6$, $R^7$ and $R^8$ are hydrogen or methyl, A is $C_1$–$C_4$-alkylene, and X is —O—.

6. A colourphotographic recording material according to claim 1, which, in addition to an optical stabiliser of the formula I, also contains one or more other optical stabilisers.

7. A colourphotographic recording material according to claim 6, which, in addition to the optical stabiliser of the formula I, also contains an ultraviolet absorber.

8. A colourphotographic recording material according to claim 1, which contains the optical stabiliser(s) in a combination with one or more colour couplers.

9. A colourphotographic recording material according to claim 1, which contains 1 to 2,000 mg of optical stabiliser per m$^2$.

* * * * *